Figure 4A:
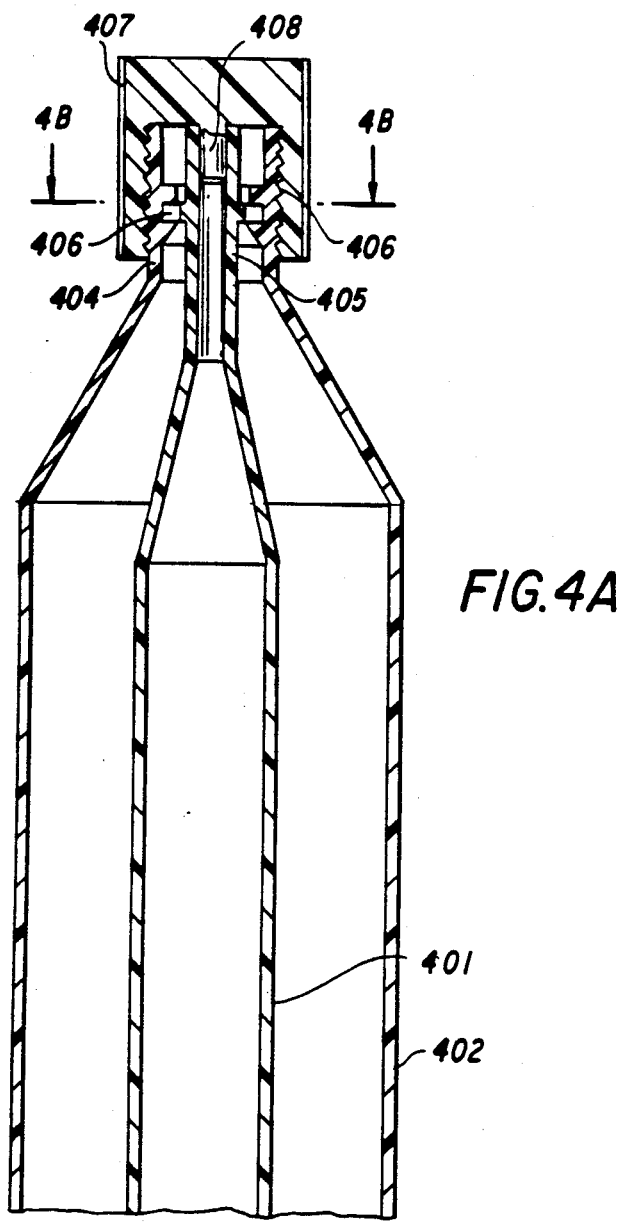

United States Patent [19]

Schaeffer

[11] Patent Number: 4,849,213

[45] Date of Patent: * Jul. 18, 1989

[54] DENTAL PREPARATION, ARTICLE AND METHOD FOR STORAGE AND DELIVERY THEROF

[76] Inventor: Hans A. Schaeffer, 18 Pallant Ave., Linden, N.J. 07036

[*] Notice: The portion of the term of this patent subsequent to Jul. 9, 2002 has been disclaimed.

[21] Appl. No.: 64,880

[22] Filed: Jun. 19, 1987

Related U.S. Application Data

[60] Division of Ser. No. 745,993, Jun. 17, 1985, Pat. No. 4,687,663, which is a continuation-in-part of Ser. No. 737,157, May 23, 1985, abandoned, which is a continuation-in-part of Ser. No. 471,188, Mar. 1, 1983, Pat. No. 4,528,180.

[51] Int. Cl.$^4$ .................... A61K 7/20; A61K 33/40
[52] U.S. Cl. ........................... 424/53; 424/78; 424/616
[58] Field of Search ............... 424/499, 253, 53, 130

[56] References Cited

U.S. PATENT DOCUMENTS

| | | | |
|---|---|---|---|
| 636,986 | 11/1899 | Heinen | 424/130 |
| 959,605 | 5/1910 | Queisser | 424/130 |
| 1,535,529 | 4/1925 | Hopkins | 424/93 |
| 1,566,218 | 12/1925 | Leland | 424/49 |
| 2,035,267 | 3/1936 | Fleischman | 424/53 |
| 2,054,742 | 9/1936 | Elbel | 424/53 |
| 2,789,731 | 4/1957 | Marraffino | 222/129 |
| 3,175,731 | 3/1965 | Ellman | 424/52 |
| 3,577,521 | 5/1971 | Scheller et al. | 424/55 |
| 3,639,574 | 2/1972 | Schmolka | 424/130 |
| 3,881,529 | 5/1975 | Mannara | 141/100 |
| 3,886,265 | 5/1975 | Evers et al. | 424/49 |
| 3,907,991 | 9/1975 | Accetta | 424/130 |
| 3,937,321 | 2/1976 | Delaney et al. | 206/84 |
| 4,098,435 | 7/1978 | Weyn | 222/94 |
| 4,211,341 | 7/1980 | Weyn | 222/94 |
| 4,223,003 | 9/1980 | Scheller | 424/49 |
| 4,330,531 | 5/1982 | Alliger | 424/53 |
| 4,487,757 | 12/1984 | Kiozpeoplou | 424/44 |
| 4,517,701 | 5/1985 | Stanford | 15/106 |
| 4,522,805 | 6/1985 | Gordon | 424/49 |
| 4,528,180 | 7/1985 | Schaeffer | 424/52 |
| 4,537,764 | 8/1985 | Pellico et al. | 424/49 |
| 4,575,375 | 3/1986 | Kozam | 604/185 |
| 4,575,457 | 3/1986 | Mazarin | 424/49 |
| 4,578,265 | 3/1986 | Pellico et al. | 424/50 |
| 4,582,701 | 4/1986 | Piechota | 424/49 |
| 4,603,045 | 7/1986 | Smigel | 424/49 |
| 4,631,185 | 12/1986 | Kim | 424/149 |
| 4,647,451 | 3/1987 | Piechota et al. | 424/49 |
| 4,687,663 | 8/1987 | Schaeffer | 424/52 |
| 4,776,500 | 10/1988 | Ford | 424/53 |

FOREIGN PATENT DOCUMENTS

| | | |
|---|---|---|
| 944506 | 4/1949 | France. |
| 1472660 | 11/1977 | United Kingdom. |
| 1565672 | 4/1980 | United Kingdom. |
| 2112642A | 7/1983 | United Kingdom. |

OTHER PUBLICATIONS

Goupil Chem. Abstracts 87th 11477h (1977) of Ger. Offen. 643,411, Apr. 07, 1977 (p. 14), (Compartmented Peroxide and Acid Toothpaste).

*Primary Examiner*—Shep K. Rose
*Attorney, Agent, or Firm*—Darby & Darby

[57] ABSTRACT

A composition useful in combatting gum disease including:

(a) a gel component including (i) about 0.1–10% by weight of hydrogen peroxide; (ii) about 0.05–5.0% by weight of a water-dispersible copolymer of acrylic acid cross-linked with polyallyl sucrose; (iii) about zero to about 2.0% by weight of a nonionic cellulose stabilizer; (iv) a neutralizing agent selected from the group consisting of sodium hydroxide, potassium hydroxide, triethanolamine, diisopropylamine and ammonia in an amount sufficient to raise the gel pH to about 3–6.0; and (v) purified water;

(b) a paste component including (i) about 2–60% sodium bicarbonate; (ii) about 1–6% of a salt selected from the group consisting of NaCl, $MgCl_2$, $MgSO_4$, $Na_2SO_4$, and $K_2SO_4$; (iii) about 2–60% of a humectant selected from the group consisting of glycerin, sorbitol, polyethylene glycol, propylene glycol, polypropylene glycol, an ethoxylated lower fatty alcohol, a propoxylated lower fatty alcohol and mixtures thereof; (iv) about 0.1–5% of a thickener stabilizer selected from the group consisting of cellulose gum, magnesium aluminum silicate and mixtures thereof; (v) about 1–30% of a stabilizing polishing agent selected from the group consisting of bentonite, titanium dioxide, silica, magnesium, oxide and mixtures thereof; and (vi) purified water; the paste component and gel component being combined immediately prior to use.

3 Claims, 4 Drawing Sheets

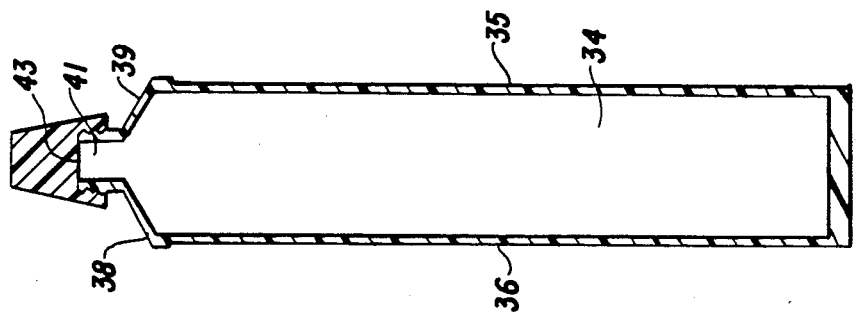
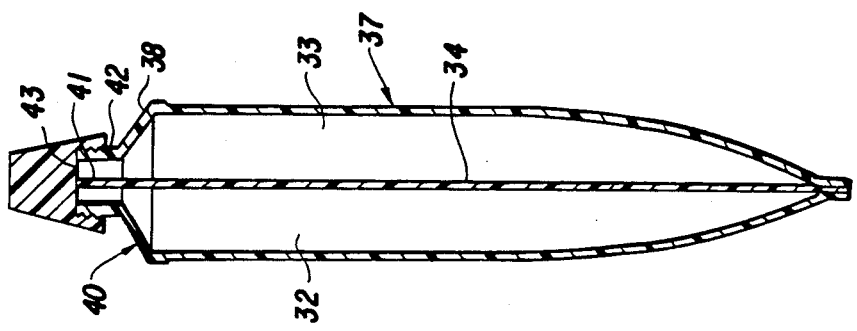
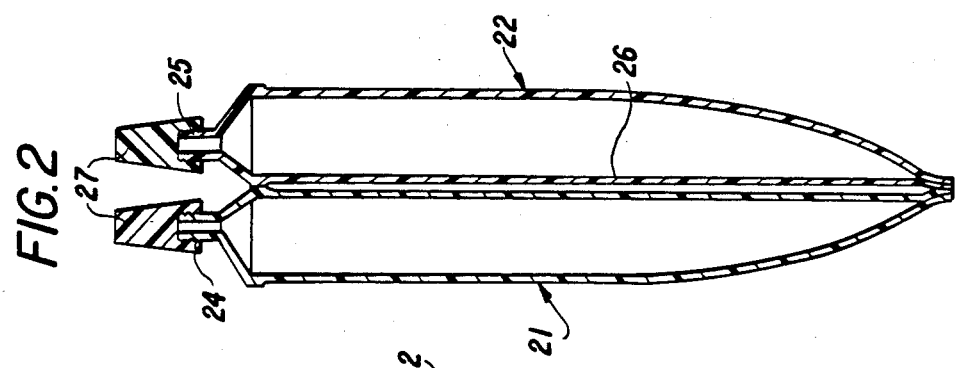
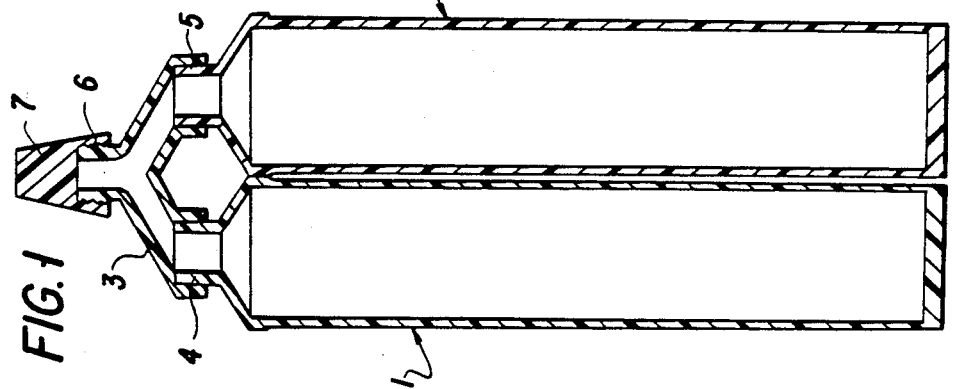

DENTAL PREPARATION, ARTICLE AND METHOD FOR STORAGE AND DELIVERY THEROF

This application is a divisional application of U.S. application Ser. No. 745,993, filed June 17, 1985 (now U.S. Pat. No. 4,687,663, the full disclosure of which is incorporated herein by reference), which was a continuation-in-part application of U.S. application Ser. No. 737,157, filed May 23, 1985 (now abandoned), which in turn was a continuation-in-part application of U.S. application Ser. No. 471,188, filed Mar. 1, 1983 (now U. S. Pat. No. 4,528,180 the full disclosure of which is incorporated herein by reference).

This invention relates to a dental preparation useful in the treatment of gum disease, to a method of storing and delivering such preparation to a use point and to an article for the storage and delivery of such preparation.

It has long been recognized that the combination of hydrogen peroxide solution with sodium bicarbonate and table salt has an excellent curative and preventive effect on gum disease caused by bacterial infection. Dr. Paul H. Keyes has advocated use of this combination to the dental profession and to the public at large based on his work of more than 25 years on the subject, which has shown that upon daily and diligent topical application of these materials, gum disease may be effectively controlled. On the basis of his recommendations, many dentists urge their patients to use the Keyes procedure (substantially as described e.g. in S. Elder: "An Alternative To Gum Surgery" Modern Maturity, Aug.–Sept. 1980 pp. 31-32).

Dr. Keyes advocates that a quantity of solid sodium bicarbonate be placed in one hand, and that the toothbrush held in the other hand, be dipped into a hydrogen peroxide -table salt solution and then transferred to the bicarbonate and applied to the teeth and gums. Upon contact with the gums, the hydrogen peroxide is exposed to the enzyme catalase, which is always present in the buccal cavity, and is attached thereby resulting in the release of active oxygen. The combination of the active oxygen and the sodium bicarbonate together with table salt destroys the bacteria responsible for gum disease. Unfortunately, hydrogen peroxide and sodium bicarbonate may not be premixed, as they immediately react and are thereby rendered ineffective against gum disease. In addition, hydrogen peroxide is unstable and therefore difficult to store for prolonged periods of time. Finally, mere dipping of the toothbrush in a hydrogen peroxide solution does not insure delivery of a sufficient amount of hydrogen peroxide to the teeth and gums. These factors are responsible for the fact that use of the Keyes procedure is extremely awkward, inconvenient and messy. Another disadvantage stems from the fact that, the mixture of hydrogen peroxide and sodium bicarbonate has a very unpleasant taste. For these reasons, patients have shown extreme reluctance to follow this procedure, especially on a daily basis, as would be required for effective gum disease control. As a result, the benefits which the Keyes procedure affords have largely been left unrealized.

Accordingly, it is an object of this invention to eliminate the above disadvantages associated with use of the Keyes procedure by providing a dental preparation incorporating the active constituents of the Keyes procedure that has pleasant taste and is neat and convenient to use, and a method for using such preparation that permits contact between hydrogen peroxide and sodium bicarbonate only shortly before use and, therefore, assures maximum effectiveness against gum disease.

It is another object of the present invention to provide a dental preparation incorporating the active constituents of the Keyes method and a method for using such preparation that permits a sufficient, consistent and reproducible amount of hydrogen peroxide to be delivered to the use point.

It is yet another object of this invention to provide an article for the storage and delivery of this improved dental preparation which makes its use neat and convenient and which prevents contact between hydrogen peroxide and sodium bicarbonate prior to application.

In accordance with the present invention, hydrogen or urea peroxide is dissolved in a nontoxic gel for use in combination with a separately stored but substantially simultaneously dispensed paste containing sodium bicarbonate, table (or another suitable) salt, and, preferably, additional cleansing, anticaries and polishing agents as well as an effective concentration of flavoring substances. Each of the gel and paste are loaded either into separate collapsible containers which are connected by means of a common orifice (as in FIG. 1), or which have substantially adjacent orifices (as in FIG. 2), or in separate compartments of a single container (as in FIGS. 3 or 4). Alternatively, the gel and paste may be loaded in separate compartments of a two-compartment pressurized container (as in FIG. 5) or a mechanically actuated pump, as in FIG. 6.

Upon substantially simultaneous squeezing of the containers, in much the same way as common toothpaste tubes (or upon actuating of the pressurized container or pump), controlled quantities of the gel and paste can be simultaneously released onto the toothbrush and immediately applied to the teeth and gums. Control of the peroxide, salt, and $NaHCO_3$ quantities delivered may be thus effected by specification of the opening of the orifice and the active ingredient concentration in each tube (or pump compartment). As described above, when the brush is applied to teeth and gums, immediate mixing of the products takes place followed by the rapid evolution of active oxygen and carbon dioxide. At the same time, the effervescence accompanying release of active oxygen activates the flavor contained in the bicarbonate paste and produces a lasting highly refreshing taste in the mouth which is unlike any other flavor provided by existing toothpastes or gels.

Another advantage afforded by the present invention, as compared with the Keyes procedure, is that a greater and more consistent amount of peroxide is delivered to the use point.

Yet another advantage stems from the tendency of the present composition to cling to the gum tissues and thus provide them with the full benefit of substantially all of the composition applied to the gums.

Gelling agents suitable for use in preparation of the peroxide gel in accordance with this invention should be nontoxic and neutral to the peroxide to assure its stability. In addition, they should be preferably sensitive to external electrolytes, such as those contained in the sodium bicarbonate paste, in order to make peroxide immediately available to the oral tissues. A gelling agent suitable for use with the present invention is a copolymer of acrylic acid cross-linked with polyallyl sucrose, as described in U.S. Pat. No. 2,798,053 issued on July 2, 1957 and assigned to B. F. Goodrich Inc.

Other gelling agents resulting in stable hydrogen (or urea) peroxide gels suitable for use in the present invention include those described in British Pat. No. 827,331, i.e, organic polymeric acid colloids including polyuronic acids, carboxypolymethylene compounds and polyester resins containing three carboxyl groups, such as partially hydrolized polyacrylates or polymethacrylates and copolymers thereof; and those described in U.S. Pat. No. 3,639,574 issued on Feb. 1, 1972 to Schmolka, i.e., polyoxyethylene polyoxypropylene block copolymers, which, according to Schmolka, may be used in the preparation of stable, firm hydrogen peroxide gels. Preferred are water-dispersible copolymers of acrylic acid cross-linked with about 0.75 to about 1.5% of polyallyl sucrose and neutralized with triethanolamine, NaOH or another alkalizing agent, as taught in U.S. Pat. No. 3,499,844[1] issued on Mar. 10, 1970 to Kibbel et al. For purposes of the present invention, Kibbel's acrylic copolymer may be preferably combined with an anionic or non-ionic surfactant, such as disclosed in U.S. Pat. No. 4,130,501[2] issued on Dec. 18, 1978 to Lutz et al. Such surfactants are not essential for the formation of a stable hydrogen peroxide gel in accordance with this invention, but may be added to facilitate distribution and rapid penetration of the active oxygen throughout the area to be treated. A particularly preferred gelling agent for the purposes of the present invention is that described by Kibbel, supra. This gelling agent may but does not have to be modified by the addition of a suitable amount of non-ionic cellulose gum such as hydroxyethyl- or hydroxypropyl-cellulose or hydroxypropyl-methyl-cellulose in order to improve the physical stability of the gel, especially when subjecting it to stress such as that resulting from squeezing of the collapsible tubes, or pumping action.

[1] The disclosures of these patents are incorporated herein by reference.

[2] The disclosures of these patents are incorporated herein by reference.

The most preferred gelling agents are marketed under the trademark CARBOPOL 941 and 1342 by Goodrich. Carbopol 941 does not need neutralization for gelling (and preferably is not neutralized in this invention) because it gels readily in the presence of hydrogen donors. Carbopol 941 has proved to have greater long term physical stability (also believed to be due to hydrogen bonding). Although Carbopol 1342 has just become available on the market and its composition and characteristics have not been fully disclosed, it is claimed by the manufacturer that this acrylic acid copolymer (even through it needs to be neutralized) displays satisfactory long term stability comparable to that of Carbopol 941.

Gels made from these agents do not need any cellulose additive as a stabilizer, because they are thixotropic (and also pseudoplastic).

Not only is Carbopol 941 the most preferred gelling agent for non-neutralized gels, it is also most preferred for neutralized gels along with Carbopol 934, 940 and 1342.

The hydrogen peroxide gel may then contain the following ingredients in the following amounts - $H_2O_2$: about 0.1–10.0% and preferably about 3.0–6.5%; Acrylic acid copolymer: about 0.05–5.0% and, preferably, about 1.0–3.0%; nonionic cellulose gum (optional): about 0–2.0% and, preferably, about 0.3–1.5%; neutralizing agent (triethanolamine, diisopropanolamine, NaOH, KOH): an amount sufficient to raise the gel pH to about 3.0–6.0; NaOH is preferred. The balance is purified (distilled or deionized) water.

If a non-neutralized gelling agent is used, the aforementioned gel may contain about 2–80% and preferably about 20–60% by weight of a polyol selected from the group consisting of glycerin, sorbitol (70% solution) polypropylene glycol, propylene glycol, polyethylene glycol, ethoxylated or propoxylated lower ($C_2$–$C_5$) fatty alcohols and mixtures thereof. The preferred polyol is glycerin. The amount of the water is decreased so that the total adds up to 100% by weight. The pH need not be controlled but falls between about 2 and 4.

The sodium bicarbonate paste contains sodium bicarbonate, sodium chloride (or another suitable salt although the salt may be omitted, if desired), purified (distilled or deionized) water, a thickener/stabilizer such as cellulose gum and or magnesium-aluminum silicate, as essential ingredients and, most preferably, it also contains a polishing/stabilizing agent, such as bentonite, silica, titanium dioxide, magnesium oxide or mixtures thereof (the first three and their mixtures are preferred). In order to disperse the "chalky" taste imparted mostly by the bicarbonate and enhance the taste and plasticity of the paste, a bodying agent is added, such as sorbitol, glycerin and/or a glycol. In addition, if the paste (in combination with the gel) is to displace toothpaste completely, additional cleansing agents, such as calcium sulfate, calcium phosphate, hydrated aluminum oxide, calcium carbonate, magnesium carbonate, and magnesium silicate or mixtures thereof can be added. A fluorine-containing compound is also preferably included for its anti-caries activity. Suitable fluorine-containing compounds are NaF, Na-monofluorophosphate, KF, potassium monofluorophosphate, sodium fluorosilicate, sodium fluorozirconate, etc. (with NaF being most preferred). Finally, a foaming agent such as sodium lauryl sulfate (most preferred), sodium N-lauroyl sarcosinate, sodium coconut monoglyceride sulfonate, sodium N-methyl-N-palmitoyl lauride or a nonionic surfactant such as a polysorbate (e.g., Tween 60 or 80 manufactured by ICI Americas, Wilmington, Delaware) or poloxamer or mixtures thereof, which also enhances the peroxide-bicarbonate-salt action, may be added. Flavoring agents, such as sodium saccharin, or other artificial sweeteners, peppermint or spearmint or other flavors are preferably added to further curb the unpleasant taste. Finally, methyl, butyl and/or propyl paraben, sodium benzoate, potassium sorbate or mixtures thereof are preferably added as preservatives, with methyl and propylparaben being most preferred. Use of a coloring agent is optional.

The constituents and quantities for the bicarbonate paste are as follows:

sodium bicarbonate: about 2–60% and preferably 20–40%;

salt: about 0–6%, preferably about 1–6% and most preferably about 2–4% of NaCl (preferred) or KCl, $MgCl_2$, $MgSO_4$, $Na_2SO_4$ or $K_2SO_4$ or mixtures thereof;

humectant: about 2–60% and preferably, 15–25% consisting of glycerin, sorbitol propylene glycol, polyethylene glycol, polypropylene glycol, ethoxylated or propoxylated lower fatty alcohols and mixtures thereof;

thickener-stabilizer: nonionic cellulose gum—about 0.1–5% and preferably 1.0–2.0%; or magnesium aluminum silicate or mixtures thereof in the same proportions;

stabilizer/polishing agent/cleanser: total about 1–30%, preferably about 1.5–20%; these preferably include one or more of: bentonite—about 0.5-7.5%; silica—about 0.1-8.0%; titanium dioxide—about 0.1-8.0%; and/or magnesium oxide—about 0.2-8.0%; preferably, about 1.5-5.0; 0.5-6.0; 0.5-3.0; and 0.5-3.0 percent, respectively.

fluorine-containing compound: sufficient to yield 200 to 3,000 ppm and preferably 1,000 to 2,000 ppm fluorine;

foaming agent: about 0.1-2.5%; preferably about 0.2-0.5%;

additional polishing agents: total about 1-30%, preferably about 5-20%;

flavoring agent(s): to taste, preferably 0.1-2%;

preservatives: about 0.05-0.5%.

The balance is purified water. A coloring agent may be added. The paste and the gel are preferably used in substantially equal proportions, by volume.

If urea peroxide is used in the gel, the bicarbonate paste composition does not change. The gel composition will be as follows:

urea peroxide: about 2-25%, preferably about 8-12%;

acrylic copolymer: about 0-3.5, preferably about 1-3%;

glycerin: balance.

The other polyols described above are reactive with the urea peroxide and should not be used.

The gel and paste combination may be simultaneously dispensed from separate collapsible tubes preferably made of plastic, or a plastic/metal laminate (to avoid reaction with $H_2O_2$) and enhanced flavor retention), such as tubes 1 and 2 shown in FIG. 1. The tubes are fitted with a Y-shaped conduit 3 which provides them with a common orifice 6. Conduit 3 may also be made of plastic (preferably by injection molding) and is preferably detachably but snugly attached to mouths 4,5 of tubes 1,2 so that it may be removed for cleaning. For additional convenience and in order to ensure dispensation of substantially equal amounts of the gel and paste, the tubes themselves may be held together, e.g., by banding or creaming, along corresponding dorsal sides, shown in FIG. 1, or, preferably, along corresponding ventral sides (see, e.g., FIG. 3A).

Alternatively, the two tubes may be constructed to have a common (preferably flat) sidewall portion 26 as shown in FIG. 2. In the latter case, the Y-shaped conduit may be unnecessary, if the mouths 24,25 of tubes 21,22 are sufficiently close so that sufficient quantities of the gel and paste may be simultaneously dispensed directly on the toothbrush. Conventional toothpaste or medicament tubes may be thus used after one of their side walls and the corresponding portion of their head structure are permanently deformed (e.g. by application of pressure) to a substantially flat surface.

A third alternative packaging method involves loading each of the gel and paste into separate compartments of the same collapsible tube, joined by a common orifice, as shown in FIG. 3. Composite tube 31 has compartments 32, 33 separated by divider 34 which is firmly attached along substantially diametrically opposed portions 35, 36 of the sidewall 37, and corresponding portions 38,39 of head structure 40. Divider 34 may be glued or welded to sidewall 37 and head structure 40 of tube 31 during manufacture of the latter. Divider 34 is preferably provided with protruding portion 41, which extends into the mouth 42 of tube 31 until its edge is substantially flush with rim 43 of mouth 42. Thus, divider 34 forms with sidewall 37 two separate compartments 32,33 of substantially the same volume for storage of the gel and paste, respectively.

In another alternative packaging method, the two tubes are "concentric" as shown in FIG. 4A. Inner tube 401 lies within and parallel with outer tube 402.

Figure 4B:
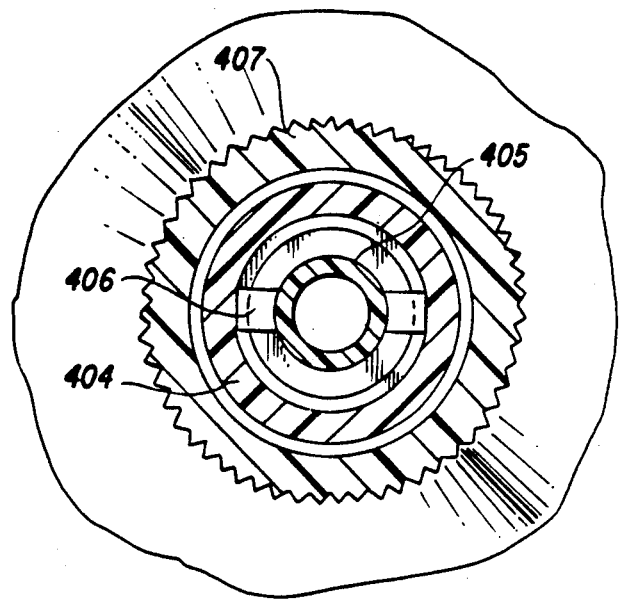

The mouths of the tubes 401 and 402, designated as 405 and 404 in FIG. 4, abut at the same point. Tube 401 is fastened on to tube 402 at the mouth by protrusion 406 (shown in enlargement in FIG. 4B, which is a cross-section of the embodiment of FIG. 4A taken along 4B—4B). Protrusions 406 are inserted in a groove of mouth 404 of tube 402. The material contained in tube 402 can still pass through the available space between mouth 404 of outer tube 402 and mouth 405 of inner tube 401. Engagement of pins 406 in the groove secures the inner tube 401 on the other tube 402.

The closure 407 of the tube-within-a-tube (which can screw on the outer tube or simply be held by pressure) arrangement may but does not have to be equipped with an interior protrusion 408 to fit in the inner tube in order to prevent premature intermixing of the two components at the mouth of the tube. Because of the pseudo-plastic quality of the gel and/or the memory of the plastic tube, however, such intermixing is not likely to occur. The tubes are filled from the bottom and are (subsequently) sealed together by conventional techniques.

Figure 5:
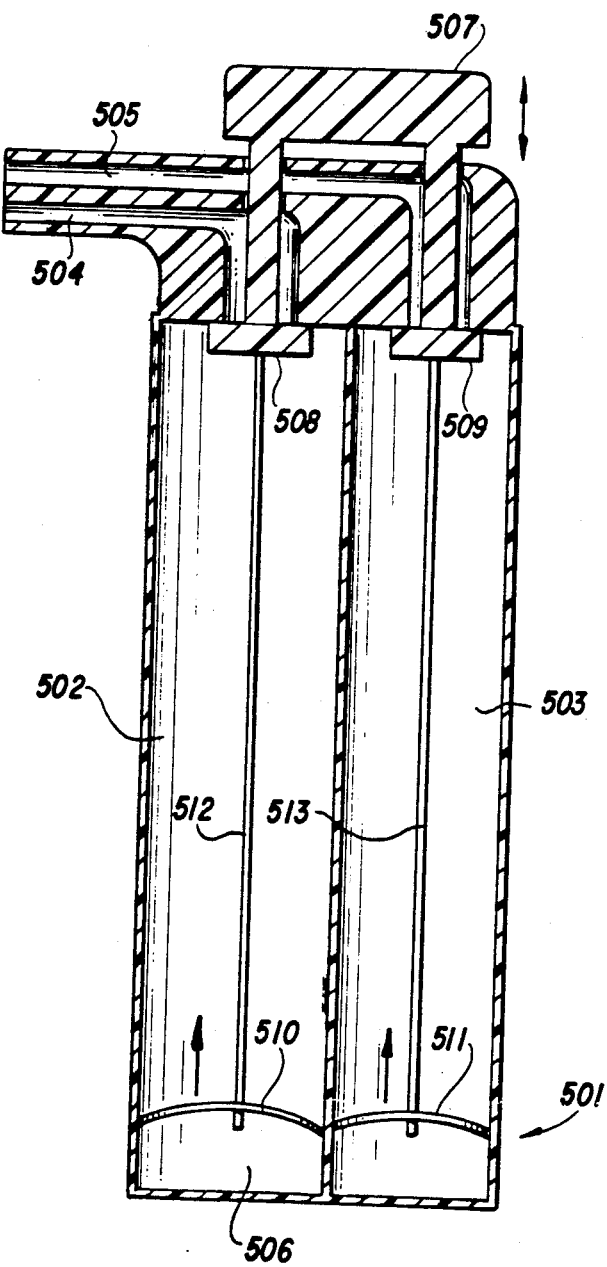
Figure 6:
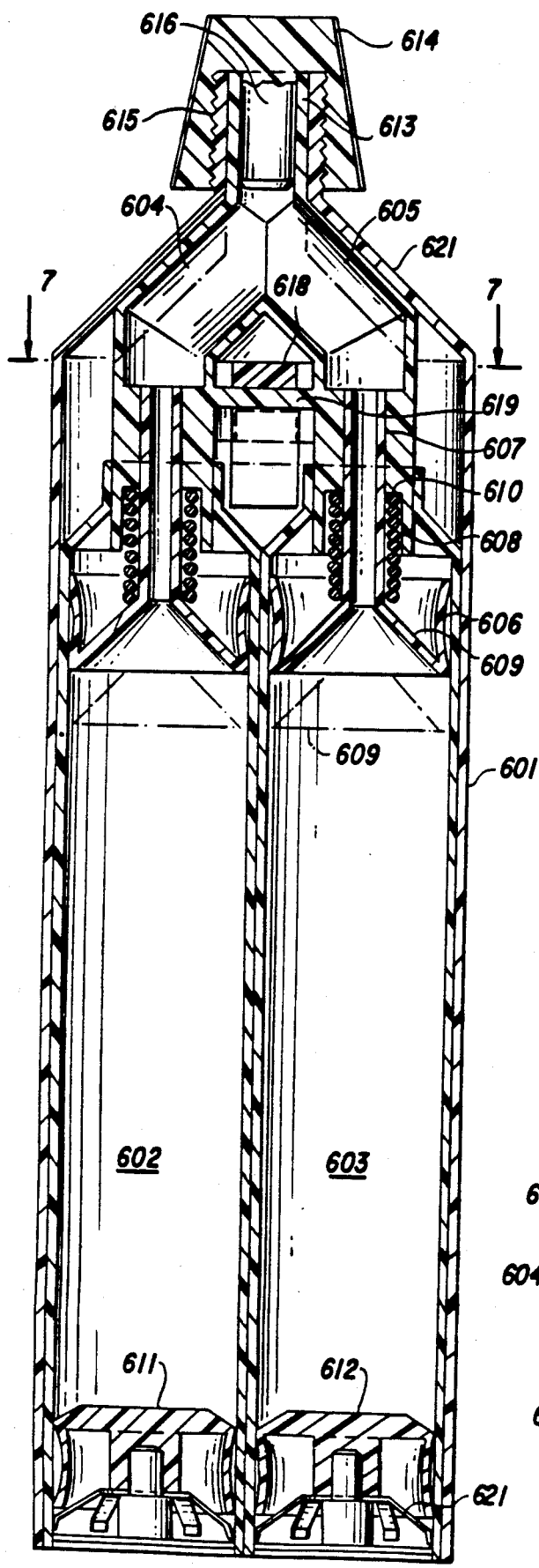

Other alternative packaging arrangements are disclosed in FIGS. 5 and 6. Pressurized container 501 in FIG. 5 is provided with two compartments 502 and 503 and two spouts 504 and 505. The internal pressure of the compartments is maintained by pressurized nitrogen, at the bottom 506 of each compartment. Operation of the mechanical actuator 507 (by pressing downwards) actuates valves 508 and 509 which release the contents of the compartments through the spouts (channels) causing the upwardly slidable sealing disks 510 and 511 (guided by members 512, 513) to move up along the compartments (due to the nitrogen being under pressure). Similar (but conventional) pressurized containers are manufactured for example by American Can Company. A dual compartment container, as described above, would be a modification of the existing containers.

Figure 7:
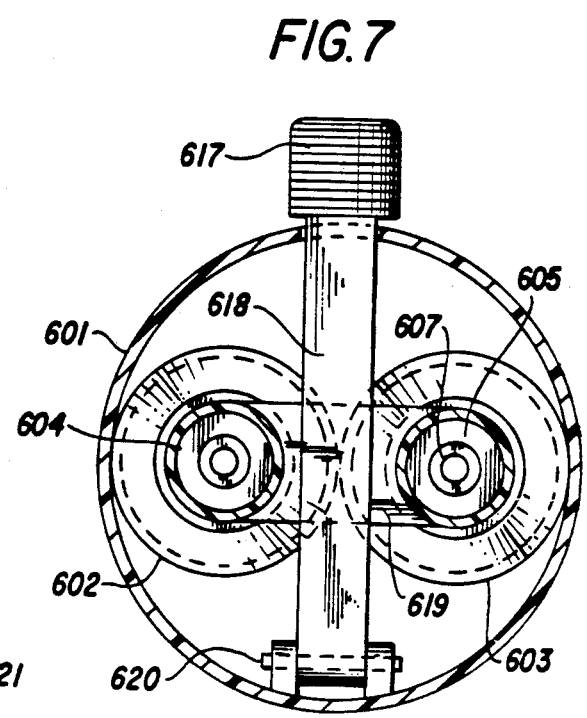

In an alternative pump embodiment depicted in FIGS. 6 and 7 a pressurized container 601 is provided with two compartments 602 and 603, and two spouts 604 and 605 for dispensing the gel and paste. Located within the tube 605 is a first piston 606 which is held in place by the upper surface of the contents within compartment 603 and a tubular extension 607 fitting within the lower portion of spout 605. A spring 608 is under compression and is held in position by the upper conical surface 609 of piston 606 and an inner shelf 601 of the spout 605. Lower pistons 611 and 612 are positioned within the lower portions of compartments 602 and 603 respectively so as to follow the dental material upwardly as it is being dispensed into the spouts 604 and 605 and eventually into nozzle 613. The upper part of container 601 has a reduced diameter to encircle the nozzle 613 and provide for a sliding engagement. Outer cap member 614 is threadedly engaged as at 615, with outer surface of nozzle 613 to effectively seal the container and prevent inadvertent dispensing of dental material as well as a pin 616 which fits snugly into open end of nozzle 613.

In operation, and with cap 614 removed, the user will depress a push button lever 617 (seen in FIG. 7) located outside the container 601. Lever 617 has substantially flat elongated member 618 which projects between spouts 604 and 605 and presses against wall 619 which bridges both spouts. Lever 617 is pivoted about pivot pin 620 affixed to inner wall of container 601. As lever 617 is depressed, member 618 will force spouts 604 and 605 downwardly and subsequently spring 608 as well as piston 606 will be lowered to phantom position (as seen in FIG. 6) causing dental material to flow upwardly within extension 607 and spout 605, mixing with material in spout 604 and through nozzle 613 to the bristles of a toothbrush. As the lever is released, the spring 608 will force nozzle 605 upwardly to its original position against conical portion 621 to container 601. The vacuum created will cause piston 606 to raise upwardly and concomitantly cause lower piston 612 to travel upwardly the distance of the expelled dental material. A spring clip 621 slideably engages inner surface of compartment 603 to allow piston to travel upwardly but be prevented from movement downwardly. Description of compartment 602 and spout 604 with its accompanying component parts operate in a like manner as described above.

The particular packaging arrangement used is not important. Those skilled in the art will be able to fashion several obvious modifications of the containers described herein by way of illustration.

Tubes, such as those suitable for use in accordance with the present invention are usually extruded around a cylindrical mandrel, cut into tube segments of suitable length, fitted with head structures and then filled from the bottom and pressed and/or welded closed, substantially as described in, e.g., U.S. Pat. No. 4,060,179 issued on Nov. 29, 1977 to McGhie, the disclosure of which is incorporated herein by reference.

In the case of the tube-within-a-tube embodiment of the present invention, the outer tube is provided first but it is not closed at the end opposite to that of the closure. The inner tube (also open-ended at the corresponding end) is inserted and fastened to the mouth of the outer tube. The two tubes are then filled and sealed together. A similar tube-within-a-tube arrangement has been proposed and described in U.S. Pat. No. 1,566,218 of Leland and issued on Dec. 15, 1925, incorporated here by reference.

The invention is further illustrated by the following specific examples which are designed merely to illustrate the present invention and not to limit its scope.

In these examples, a hydrogen peroxide gel containing 3–6.5% hydrogen peroxide by weight, useful for simultaneous administration with a sodium bicarbonate paste is prepared as follows:

EXAMPLE 1

| Ingredients | |
| --- | --- |
| Hydrogen peroxide, 35% aqueous solution (5% $H_2O_2$ in final gel) | 14.3 parts |
| Purified water | 84.45 |
| Copolymer of acrylic acid crosslinked with 1% by weight of polyallyl sucrose having 5.8 allyl groups per molecule (CARBOPOL 934 made by B. F. Goodrich Chemical Co., Akron, Ohio) | 0.5 |
| Hydroxyethyl cellulose | 0.5 |
| Triethanolamine | 0.25 |

The gel is prepared by combining the hydrogen peroxide solution with the purified water, followed by the gradual addition of CARBOPOL 934. Upon thorough dispersion of the copolymer hydroxyethyl cellulose is slowly added and dissolved. Finally, triethanolamine is added, forming a clear, homogeneous, stable and viscous gel having a pH of 3.4.

EXAMPLE 2

| Ingredients | |
| --- | --- |
| Hydrogen peroxide, 35% aq. solution (3.5% $H_2O_2$ in final gel) | 10.0 parts |
| Distilled or deionized water | 88.9 |
| Acrylic acid copolymer CARBOPOL 940 (Goodrich) | 0.6 |
| Hydroxyethylcellulose | 0.5 |
| Sodium hydroxide, 10% solution    q.s. | pH 3.8–4.0 |

Preparation: same as that of Example 1.

EXAMPLE 3

| Ingredients | |
| --- | --- |
| Hydrogen peroxide, 35% (3.5% $H_2O_2$ in final gel) | 10.0 parts |
| Distilled or deionized water | 89.0 |
| Acrylic acid copolymer - CARBOPOL 941 (Goodrich) | 0.7 |
| Hydroxypropylcellulose | 0.3 |
| Sodium hydroxide, 10% solution    q.s. | pH 3.8–4.0 |

Preparation: same as that of Example 1.

EXAMPLE 4

| Ingredients | |
| --- | --- |
| Hydrogen peroxide, 35% (4.0% $H_2O_2$ in final gel) | 11.5 parts |
| Distilled or deionized water | 86.65 |
| Acrylic acid copolymer - CARBOPOL 934 (Goodrich) | 0.75 |
| Sodium laurylsulfate, dentifrice grade | 0.50 |
| Hydroxypropylcellulose | 0.6 |
| Sodium hydroxide, 10% solution    q.s. | pH 3.5–4.5 |

Preparation:
The hydrogen peroxide solution is combined with the distilled or deionized water. Sodium laurylsulfate is added under constant agitation and dissolved. Gradually, CARBOPOL 934 is added and dispersed. Hydroxypropylcellulose is added in increments and dissolved. When the mixture is homogeneous, sodium hydroxide is added slowly to the desired pH level and viscosity.

EXAMPLE 5

| Ingredients | |
| --- | --- |
| Hydrogen peroxide, 35% (6.0% $H_2O_2$ in final gel) | 17.14 parts |
| Distilled or deionized water | 81.76 |
| Acrylic acid copolymer - CARBOPOL 940 (Goodrich) | 0.70 |
| Hydroxyethylcellulose | 0.40 |
| Sodium hydroxide, 10% solution    q.s. | pH 3.5–4.0 |

Preparation: same as that of Example 1.

EXAMPLE 6

| Ingredients | |
| --- | --- |
| Hydrogen peroxide, 35% (3.0% $H_2O_2$ in final gel) | 8.58 parts |

-continued

| Ingredients | |
|---|---|
| Distilled or deionized water | 89.22 |
| Acrylic acid copolymer - CARBOPOL 934 (Goodrich) | 0.70 |
| Hydroxypropyl methylcellulose | 0.65 |
| Nonionic surfactant PLURONIC F 127 (BASF Corp., New Jersey) | 0.85 |
| Sodium hydroxide, 10% solution   q.s. | pH 3.5–4.5 |

Preparation: same as that of Example 4.

EXAMPLE 7

The sodium bicarbonate paste is prepared as follows:

| Ingredients | |
|---|---|
| Deionized water | 31.94 parts |
| Sorbitol 70% solution, USP | 20.0 |
| Cellulose gum - CMC 7MF (Hercules) | 1.44 |
| Sodium saccharin | 0.20 |
| Magnesium aluminum silicate - VEEGUM F (made by R. T. Vanderbilt Co., Inc., Norwalk, Conn.) | 1.17 |
| Sodium bicarbonate, fine powder | 40.00 |
| Sodium chloride | 4.00 |
| Sodium lauryl sulfate - dentifrice grade | 0.30 |
| Peppermint/Spearmint Flavor | 0.75 |
| Methyl paraben, USP | 0.15 |
| Propyl paraben, USP | 0.05 |

Procedure:
Glycerin and propylene glycol are combined in a first container with agitation. Cellulose gum is added and dispersed thoroughly throughout the mixture. Saccharin, methylparaben and propylparaben are added to the required amount of purified water in a separate container and heated to dissolve. VEEGUM is added and the mixture is agitated until uniform. The contents of the first container are slowly added to the second container and the final mixture is agitated thoroughly until uniform. Flavoring agent, sodium lauryl sulfate and coloring (if desired) are added and the paste is agitated at moderate speed until uniform. Entrapped air is removed by degassing in a vacuum vessel. Further homogeneity may be obtained by milling, if necessary.

EXAMPLE 8

| Ingredients | |
|---|---|
| Deionized water | 33.43 part |
| Glycerin | 10.00 |
| Propylene glycol | 10.0 |
| Cellulose gum - CMC 7MF (Hercules) | 1.45 |
| Sodium saccharin | 0.20 |
| Magnesium aluminum silicate - VEEGUM F | 1.17 |
| Sodium bicarbonate, fine powder | 25.00 |
| Dicalcium phosphate dihydrate | 13.50 |
| Dicalcium phosphate, anhydrous | 1.50 |
| Sodium chloride | 2.50 |
| Sodium lauryl sulfate, dentifrice grade | 0.30 |
| Methylparaben, USP | 0.15 |
| Propylparaben, USP | 0.05 |
| Peppermint/Spearmint Flavor | 0.75 |
| FD & C Blue No. 1, 0.1% solution | q.s. |
| DS & C Yellow No. 6, 0.1% solution | q.s. |

EXAMPLE 9

Paste containing fluoride:

| Ingredients | |
|---|---|
| Deionized water | 33.51 |
| Sorbitol, 70% solution | 20.00 |
| Sodium saccharin | 0.20 |
| Cellulose gum CMC 7MF (Hercules) | 1.54 |
| Magnesium aluminum silicate - VEEGUM F | 1.17 |
| Sodium fluoride | 0.33 |
| Methyl paraben, USP | 0.15 |
| Propyl paraben, USP | 0.05 |
| Calcium sulfate | 10.00 |
| Sodium bicarbonate | 25.00 |
| Sodium chloride | 2.00 |
| Hydrated aluminum oxide | 5.00 |
| Peppermint/Spearmint Flavor | 0.75 |
| Sodium lauryl sulfate | 0.30 |

Procedure: Same as that of Example 8.

EXAMPLE 10

Peroxide Gels

| Composition 10-A | |
|---|---|
| Hydrogen peroxide, 35% aqueous solution (4.0% $H_2O_2$ in final gel) | 11.5 |
| Distilled water | 86.6 |
| Acrylic acid copolymer - Carbopol 934 (Goodrich) | 1.5 |
| Sodium lauryl sulfate, dentifrice grade | 0.1 |
| Hydroxypropyl cellulose | 0.3 |
| Sodium hydroxide, 10% solution   q.s. | pH 3.0–4.5 |
| Composition 10-B | |
| Hydrogen peroxide, 35% (4.0% $H_2O_2$ in final gel) | 11.5 |
| Distilled water | 88.0 |
| Acrylic acid copolymer (Carbopol 934, 940, 941, or 1342) | 1.5 |
| Sodium hydroxide, 10% solution   q.s. | pH 3.0–4.5 |
| Composition 10-C | |
| Hydrogen peroxide, 35% (4.0% $H_2O_2$ in final gel) | 11.5 |
| Distilled water | 46.0 |
| Glycerin, anhydrous | 40.0 |
| Acrylic acid copolymer - Carbopol 941 | 2.5 |

Methods of preparation

Composition 10-A: same as listed in Example 4

Composition 10-B: same as in Example 4 except that sod. lauryl sulfate and hydroxypropyl cellulose were omitted. The composition including Carbopol 1342 has not been actually made.

Composition 10-C: The glycerin and water were combined and heated to 50°–60° C. Very slowly, Carbopol 941 was added under constant agitation.

When a clear gel had formed and no undissolved lumps remained, the gel was cooled to 25° C. and the hydrogen peroxide was added. Agitation was maintained until the mixture became homogeneous. The gel was de-aerated in a vacuum vessel.

EXAMPLE 11

Sodium bicarbonate Paste

| Composition 11-A | |
|---|---|
| Glycerin | 25.0 |
| Cellulose gum CMC 7MF (Hercules) | 1.54 |
| Deionized water | 32.71 |
| Magnesium aluminum silicate Veegum (R. T. Vanderbilt) | 1.10 |
| Sodium saccharin | 0.60 |
| Sodium chloride | 2.0 |
| Methyl paraben | 0.15 |
| Propyl paraben | 0.05 |
| (Sodium hydroxide solution 10%, q.s. pH 8.0–8.5, may be added, if necessary for pH adjustment) | |

| -continued | |
|---|---|
| Sodium fluoride | 0.22 |
| Bentonite | 4.0 |
| Titanium dioxide | 2.0 |
| Silica | 4.0 |
| Sodium bicarbonate | 25.0 |
| Flavor (spearmint) | 1.0 |
| Sodium lauryl sulfate | 0.3 |
| Color (FDC Blue No. 1) q.s. | |

Method of preparation

The cellulose gum was added to the glycerin and dispersed thoroughly.

In a separate vessel, the parabens, sodium saccharin and sodium chloride were dissolved in water at 60°-70° C. To the clear solution was added the Veegum and the mixture was agitated until uniform. The pH of this solution was determined to be 8.0-8.5 (and adjusted, if necessary).

The gum dispersion was added to the Veegum solution and agitated until uniform.

To the blend were added the powders, bentonite, $TiO_2$, silica, $NaHCO_3$, and NaF, under vigorous agitation.

To the paste were added flavor, sodium lauryl sulfate and color.

The finished paste is milled and degassed in a vacuum vessel.

EXAMPLE 13

Urea peroxide gel

| Composition 13-A | |
|---|---|
| Urea peroxide (35% $H_2O_2$ equivalent) | 10.0 parts by weight |
| Glycerin, anhydrous | 90.0 |

Method: Urea peroxide is slowly added under agitation to the anhydrous glycerin until a clear gel is formed which has s suitable consistency for filling into collapsible tubes.

| Composition 13-B | |
|---|---|
| Urea peroxide | 10.0 |
| Acrylic acid copolymers - Carbopol 941 | 1.5 |
| Glycerin, anhydrous | 88.5 |

The method is the same as that for 13-A except the urea peroxide and Carbopol 941 are both added to the glycerin solution.

Although the present invention has been described with reference to preferred embodiments, those of ordinary skill in the art will readily appreciate that many additions, deletions, modifications and substitutions are possible within the spirit of the present invention and the scope of the following claims.

What is claimed is:

1. A composition useful in combatting gum disease comprising:
    (a) a gel component comprising (i) about 0.1-10% by weight of hydrogen peroxide; (ii) about 0.05-5.0% by weight of a water-dispersible copolymer of acrylic acid cross-linked with polyallyl sucrose; (iii) about zero to about 2.0% by weight of a nonionic cellulose stabilizer; (iv) a neutralizing agent selected from the group consisting of sodium hydroxide, potassium hydroxide, triethanolamine, diisopropylamine and ammonia in an amount sufficient to raise the gel pH to about 3-6.0; and (v) purified water;
    (b) a paste component comprising: (i) about 2-60% sodium bicarbonate; (ii) about 0-6% of a salt selected from the group consisting of NaCl, KCl, $MgCl_2$, $MgSO_4$, $Na_2SO_4$, and $K_2SO_4$; (iii) about 2-60% of a humectant selected from the group consisting of glycerin, sorbitol, polyethylene glycol, propylene glycol, polypropylene glycol, an ethoxylated lower fatty alcohol, a propoxylated lower fatty alcohol and mixtures thereof; (iv) about 0.1-5% of a thickener stabilizer selected from the group consisting of cellulose gum, magnesium aluminum silicate and mixtures thereof; (v) about 1-30% of a stabilizing polishing agent selected from the group consisting of bentonite, titanium dioxide, silica, magnesium oxide and mixtures thereof; and (vi) purified water; said paste component and gel component being combined immediately prior to use.

2. The composition of claim 1, wherein said gel component comprises about 3.0-6.5% hydrogen peroxide; about 1-3% of said copolymer; and about 0.3-1.5% of said neutralizing agent.

3. The composition of claim 2, wherein said paste component comprises about 20-40% of said sodium bicarbonate; about 2-4% of said salt; about 15-255 of said humectant; about 1.0-2.0% of said stabilizer; and about 1.5-20% of said stabilizing polishing agent.

* * * * *